United States Patent [19]

Detweiler

[11] Patent Number: 5,141,516
[45] Date of Patent: Aug. 25, 1992

[54] DISSOLVABLE ANASTOMOSIS STENT AND METHOD FOR USING THE SAME

[76] Inventor: Mark B. Detweiler, via Udino Bombieri 26, 00062 Bracciano (Rome), Italy

[21] Appl. No.: 555,343

[22] Filed: Jul. 19, 1990

[30] Foreign Application Priority Data

Jul. 26, 1989 [IT] Italy ................. 48240 A/89
May 16, 1990 [IT] Italy ................. 47968 A/90

[51] Int. Cl.$^5$ ............................................. A61B 17/00
[52] U.S. Cl. ................................ 606/154; 606/153; 606/214
[58] Field of Search ............... 606/153, 154, 214, 213

[56] References Cited

U.S. PATENT DOCUMENTS

| | | | |
|---|---|---|---|
| 3,683,926 | 8/1972 | Suzuki | 606/154 |
| 4,705,039 | 11/1987 | Sakaguchi et al. | 606/154 |
| 4,055,186 | 10/1977 | LeVeen | 606/153 |
| 4,552,142 | 11/1985 | Hardy, Jr. et al. | 606/154 |
| 4,899,744 | 2/1990 | Fujitsuka et al. | 606/153 |

OTHER PUBLICATIONS

Senn, N., "Enterorrhaphy; Its History, Technique and Present Status," *J.A.M.A.*, 21(7):215–235 (1893).
Hjortrup, A. P. et al., "Fibrin Adhesive Versus Sutured Anastomosis: A Comparative Intra-Individual Study in the Small Intestine of Pigs," *Br. J. Surg.*, 73:760–761 (1986).
Ethicon, Inc. brochure entitled "PROXIMATE TM ILS Disposable Intraluminal Stapler System".
Murphy, J. B., "Cholecysto-Intestinal, Gastro-Intestinal, Entero-Intestinal Anastomosis, and Appoximation Without Sutures," *Medical Record*, 42:665–676 (Dec. 10, 1892).
Hardy, T. Jr. et al., "A Biofragmentable Ring for Sutureless Bowel Anastomosis An Experimental Study", *Dis. Colon Rectum*, 28:484–490 (1985).
Hardy, T., Jr. et al., "Initial Clinical Experience with a Biofragmentable Ring for Sutureless Bowel Anastomosis", *Dis Colon Rectum*, 30:55–61 (1987).
Maney, J. et al., "Biofragmentable Bowel Anastomosi Ring: Comparative Efficacy Studies in Dogs," *Surgery*, 103:56–62 (1988).
Cahill, C.J. et al., "Sutureless Large Bowel Anastomosis: European Experience with the Biofragmentable Anastmosis Ring," *Br. J. Surg.*, 76:44–347 (1989).
Kamiji, T. et al., "*Microvascular Anastomosis Using Polyethylene Glycol 4000 and Fibrin Glue,*" *British Journal of Plastic Surgery*, 42:54–58 (1989).

*Primary Examiner*—Stephen C. Pellegrino
*Assistant Examiner*—Gary Jackson
*Attorney, Agent, or Firm*—Panitch Schwarze Jacobs & Nadel

[57] ABSTRACT

A dissolvable anastomosis stent comprises a first member for receiving a first vessel stump, a second member for receiving a second vessel stump, and engaging means for engaging the first and second members where the engaging means and members are constructed of a biocompatible, non-toxic material which substantially completely dissolves mammalian bodily fluids. In addition, methods for preparing the dissolvable anastomosis stent and methods for surgical mammalian anastomoses using the dissolvable anastomosis stent are disclosed.

11 Claims, 4 Drawing Sheets

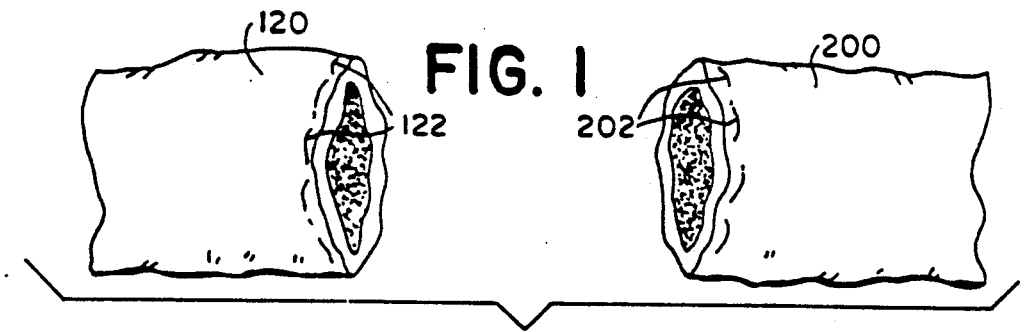
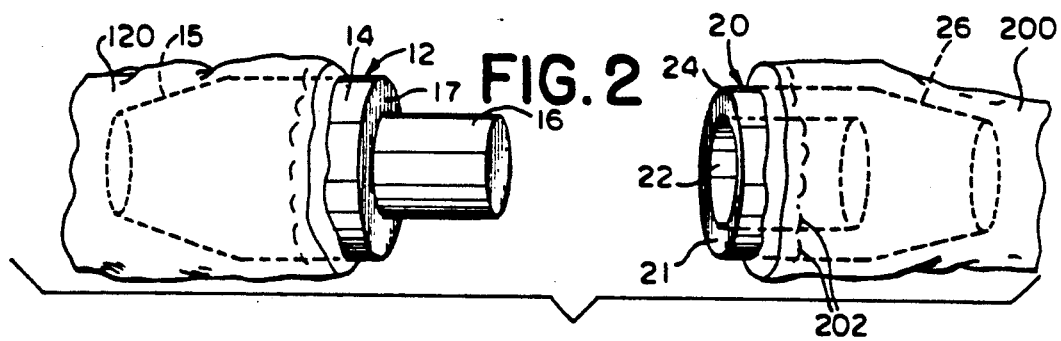
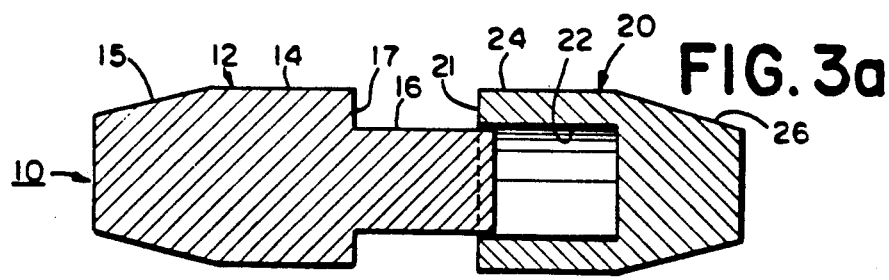
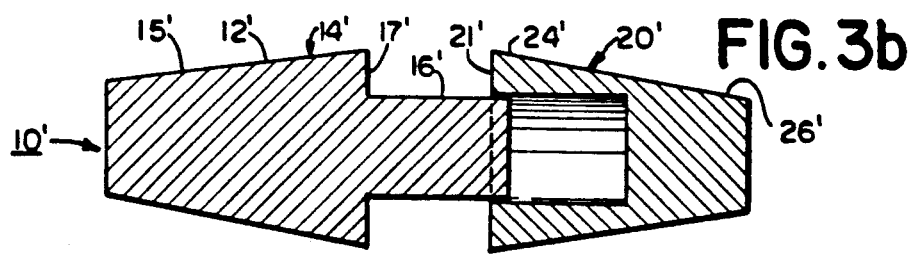
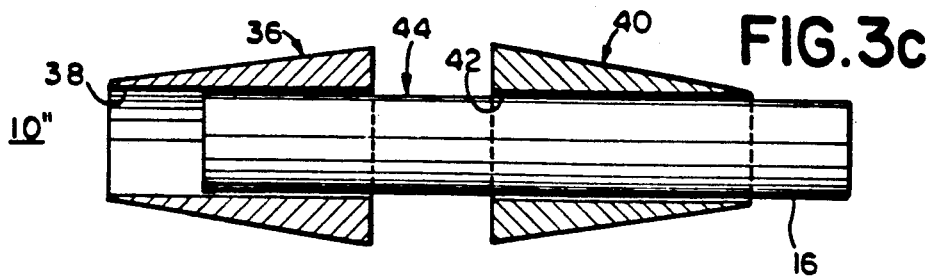

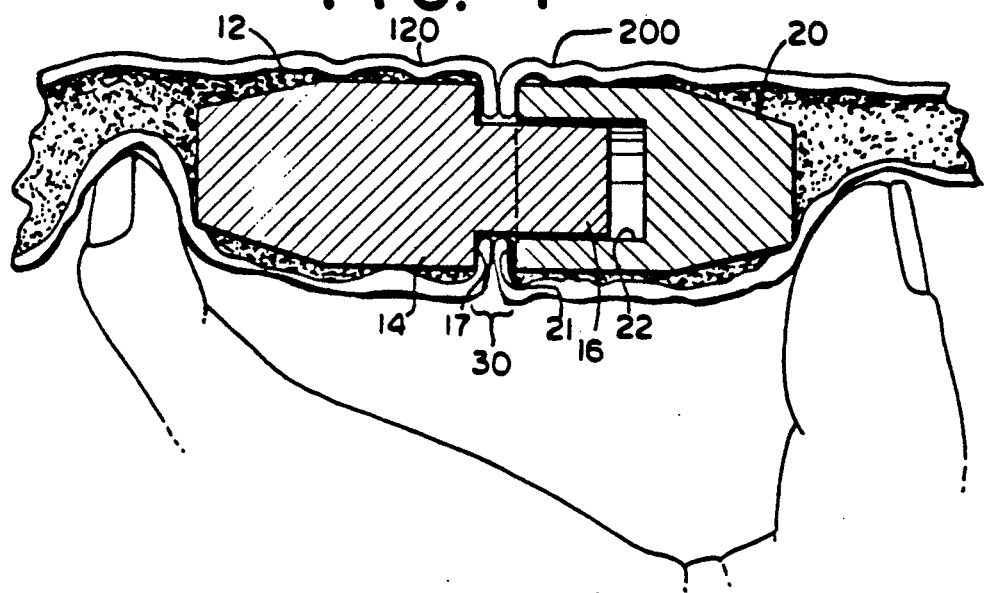
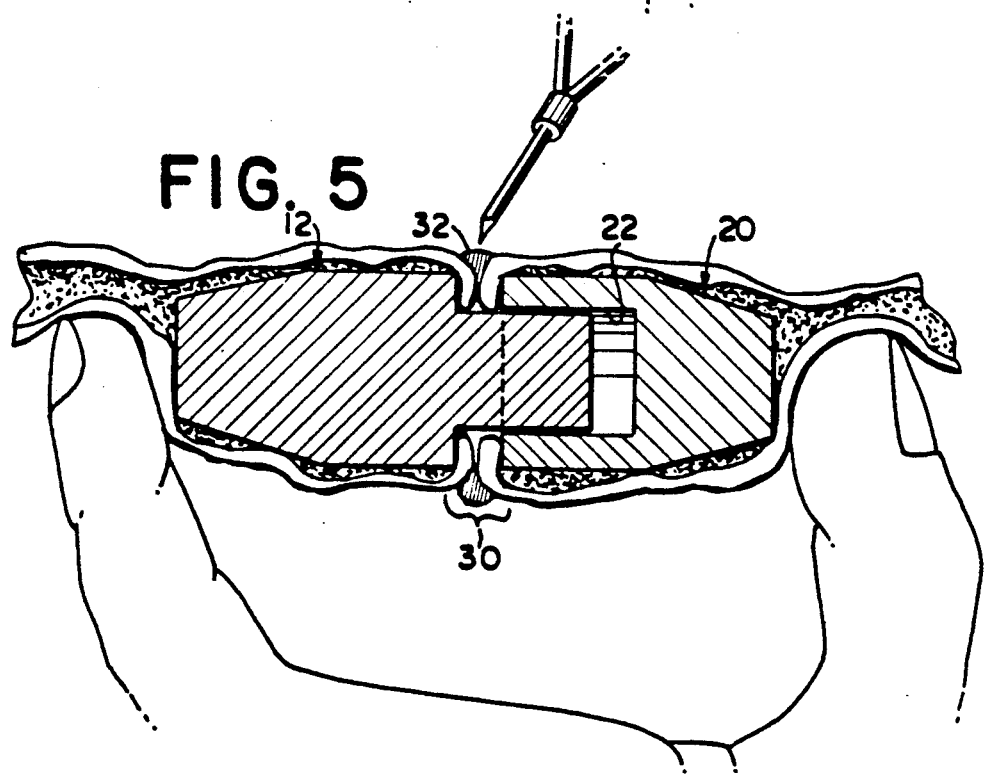

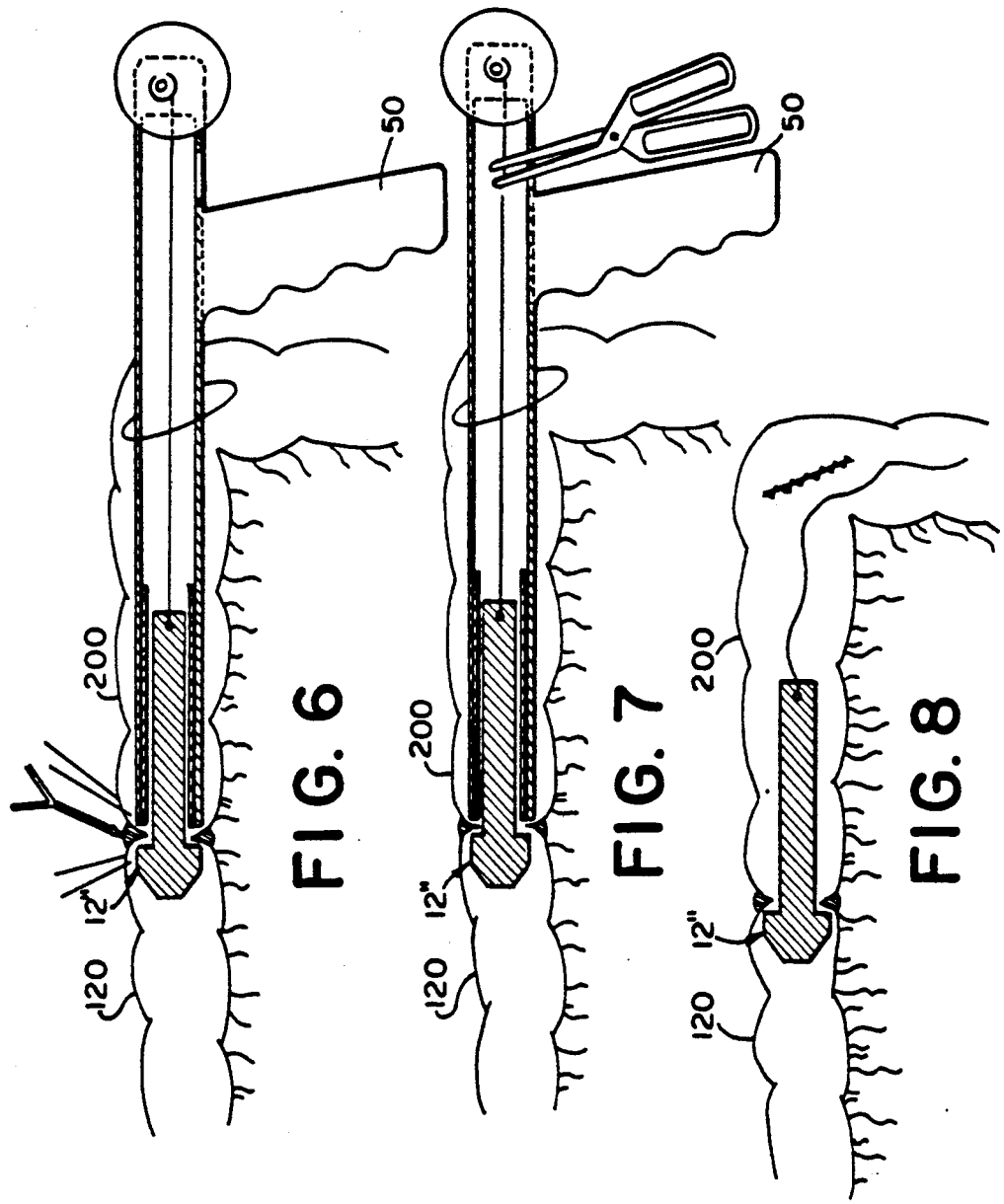

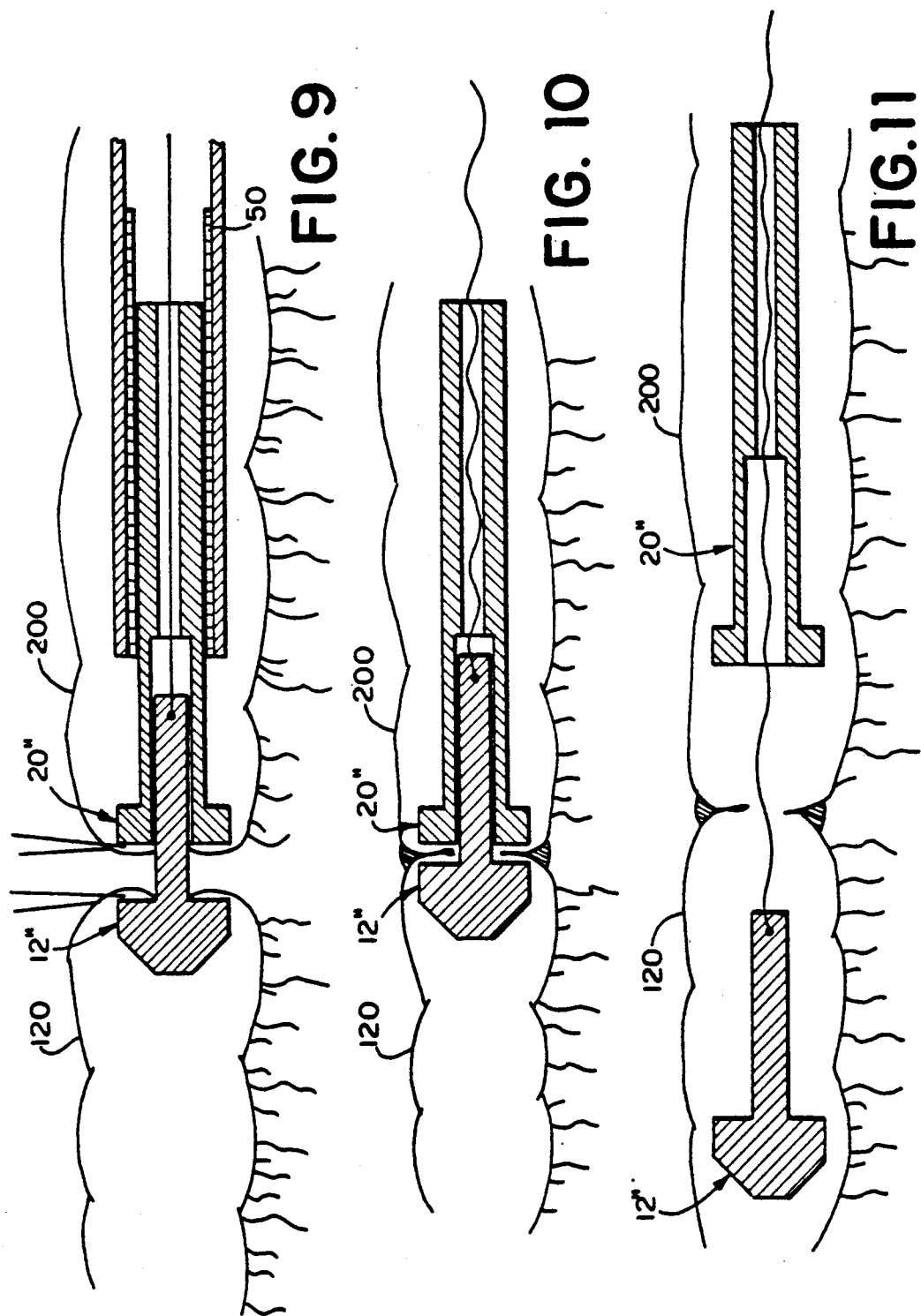

DISSOLVABLE ANASTOMOSIS STENT AND METHOD FOR USING THE SAME

BACKGROUND OF THE INVENTION

The present invention relates to dissolvable intraluminal stents for mammalian anastomoses.

Surgical anastomosis is the procedure of choice to relieve or correct blocked or otherwise inoperative luminal vessels. The most common vessel to which this procedure is applied is the intestine, but the procedure may also be used to correct abnormalities in blood vessels, biliary and urinary ducts, for example, as well as other vessels. However, it has been long recognized that there is a need for an essentially sutureless procedure. As early as 1892, J. B. Murphy reported sutureless anastomosis procedures using what he called an anastomosis button. J. B. Murphy "Cholecysto-Intestinal, Gastro-Intestinal Entero-Intestinal Anastomosis, An Approximation Without Sutures," *Medical Record*, 42(24):665-76 (Dec. 10, 1892). The techniques described by Murphy were adopted by the medical community for decades and the button became commonly called the "Murphy button." The Murphy button generally comprised a two-part metal snap which, when snapped or screwed together, would hold the two vessel stumps in close proximity until scar tissue joined the two stumps. However, one major disadvantage was that the button, when used in intestinal anastomosis procedures, would either pass several days after the surgical procedure, causing great discomfort, or would become lodged in the intestinal lumen, causing serious blockage. In addition, necrosis at the anastomosis site was prevalent when using the Murphy button.

More recently, sophisticated variants of the Murphy button have been developed and are commonly called the bowel anastomosis ring (BAR). Much of the early work of the BAR was performed and reported by T. G. Hardy et al., "A Biofragmentable Ring for Sutureless Bowel Anastomosis", *Dis. Col. & Rect.*, 28:484-90 (1985), with later work by Hardy and others. T. G. Hardy et al., "Initial Clinical Experience With a Biofragmentable Ring for Sutureless Bowel Anastomosis," *Dis. Col. & Rect.*, 30:55-61 (1987); J. W. Maney et al., "Biofragmentable Bowel Anastomosis Ring: Comparative Efficacy Studies in Dogs," *Surgery*, 103(1):56-62 (1988); C. J. Cahill et al. "Sutureless Large Bowel Anastomosis: European Experience With the Biofragmentable Anastomosis Ring," *Br. J. Surg.*, 76(4):344-47 (1989). The BAR functions similarly to the Murphy button by holding two vessel stumps in contact with one another after securing each of the vessel stumps to the BAR with a purse-string suture and snapping the two BAR pieces together.

The BAR is fashioned from a composition that fragments under normal intraluminal conditions and these BAR fragments are expelled several days to one or two weeks after implantation. However, these fragments are irregular and sharp and are generally several millimeters to over 2 centimeters in length, thereby causing discomfort when passed. In addition, the BAR anastomosis procedure requires that purse-string sutures be in and remain in the vessel stumps to attach the vessel stumps to the BAR after the surgical procedure has been completed. These sutures may remain in the vessel tissue for several days to several weeks and their presence increases the risk of infection or leakage and edema. Moreover, despite efforts to decrease necrosis at the anastomosis, primarily accomplished by providing the BAR with interdigitating parts which lock at various gap sizes, necrosis still occurs at the site of purse-string sutures following the BAR procedure.

The present invention overcomes the inefficiencies and deficiencies of the prior art by virtue of an improved anastomosis stent for anastomosis procedures which simplifies the surgical procedure and lessens the surgical complications and postoperative discomfort to the patient.

SUMMARY OF THE INVENTION

According to one aspect of the present invention, a dissolvable stent for mammalian anastomoses comprises a first member for receiving a first vessel stump, a second member for receiving a second vessel stump, and engaging means for engaging the first and second members where the first and second members and the engaging means are constructed of a biocompatible, non-toxic material which substantially completely dissolves in mammalian bodily fluids.

Another aspect of the present invention is a dissolvable stent for mammalian anastomoses comprising a male member having a first end with a first circumference and a second end with a second circumference smaller than the first circumference, and a female member having first and second ends and a circumference at least partially substantially the same as the first circumference of the male member and an inner circumference for at least partially receiving the male member where the male and female members of the stent are axially aligned when the second end of the male member is received by the female member.

A further aspect of the present invention is a method of manufacturing a dissolvable stent for mammalian anastomoses comprising the steps of dissolving a biocompatible, non-toxic solid material in a biocompatible, non-toxic liquid at a temperature sufficient to form a liquid solution, pouring the liquid solution into a first mold having a shape complementary to a male member for receiving a first vessel stump, pouring the liquid solution into a second mold having a shape complementary to a female member for receiving a second vessel stump, solidifying the liquid solution in the first and second molds to form solidified male and female members in the first and second molds, respectively, and removing the solidified male and female members from the molds.

Yet another aspect of the present invention is a method of surgical mammalian vessel anastomosis using the dissolvable stent comprising the steps of circumferentially inserting a first purse-string suture into the first vessel stump and a second purse-string suture into the second vessel stump where the first and second purse-string sutures are positioned proximate the edges on the first and second vessel stumps, inserting the first end of the male member of the stent into the opening of the first vessel stump and inserting the second end of the female member of the stent into the opening of the second vessel stump, inserting the second end of the male member of the stent partially into the first end of the female member of the stent, tightening the purse-string sutures to annularly introflect the edges of the first and second vessel stumps onto the second end of the male member of the stent, and inserting the second end of the male member of the stent farther into the female member of the stent to cause the annularly introflected edge of the first vessel stump to engage the annularly introflected edge of the second vessel stump to form a substantially annular engagement region with a clamping force sufficient to maintain the edges of the stumps in the annular engagement region between the male and female members.

BRIEF DESCRIPTION OF THE DRAWINGS

The foregoing summary of the invention, as well as the following detailed description of preferred embodiments will be better understood when read in conjunction with the appended drawings. For the purpose of illustrating the invention, there is shown in the drawings embodiments which are presently preferred, it being understood, however, that the invention is not limited to the specific arrangements and instrumentalities disclosed. In the drawings:

FIG. 1 is a side elevational view of two vessel stumps having purse-string sutures therein;

FIG. 2 is a side elevational view of two vessel stumps having male and female members of a dissolvable stent according to the present invention inserted therein;

FIG. 3a is a cross-sectional view along a longitudinal axis of the embodiment of a dissolvable stent for mammalian anastomoses according to the present invention illustrated in FIG. 2;

FIG. 3b is a cross-sectional view along a longitudinal axis of another embodiment of a dissolvable stent according to the present invention;

FIG. 3c is a partial cross-sectional view along a longitudinal axis of still another embodiment of a dissolvable stent for mammalian anastomoses according to the present invention;

FIG. 4 is a partial cross-sectional view along a longitudinal axis showing a dissolvable stent inserted into two vessel stumps during one embodiment of a surgical anastomosis procedure in accordance with the present invention;

FIG. 5 is a partial cross-sectional view along a longitudinal axis showing the anastomosis procedure of FIG. 4 at a later stage;

FIGS. 6 through 8 are schematic diagrams illustrating a second embodiment of a surgical anastomosis procedure using the dissolvable stent in accordance with the present invention using an insertion device.

FIGS. 9 through 11 are schematic diagrams illustrating a third embodiment of a surgical anastomosis procedure using the dissolvable stent in accordance with the present invention using an insertion device.

DETAILED DESCRIPTION OF PREFERRED EMBODIMENTS

Referring to the drawings, wherein like numerals indicate like elements throughout the several views, there is shown in FIGS. 2 and 3a a dissolvable stent 10 for mammalian anastomoses in accordance with the present invention. The stent 10 comprises a first or male member 12 for receiving a first vessel stump 120 and a second or female member 20 for receiving a second vessel stump 200. The first member 12 preferably has an integrally formed engaging means or projecting portion 16 engageable within a cavity 22 formed in the second member 20, preferably by slidable insertion along the central longitudinal axis of the members as seen in FIGS. 3a and 5.

Other embodiments of basic versions of a dissolvable stent according to the present invention are illustrated as stents 10' and 10" in FIGS. 3b and 3c, respectively.

Since stent 10' is very similar to the construction of stent 10, the numerals representing components of FIG. 3b are primed compared to those components of FIGS. 2 and 3a having similar functions. Still other embodiments according to the present invention illustrated in FIGS. 6 through 11, comprise a dissolvable stent and a removable stent insertion tool 50.

The stents according to the present invention are constructed of a biocompatible, non-toxic material which substantially completely dissolves in mammalian bodily fluids. The stent serves the purpose of an intraluminal support for vessel anastomoses and, in such capacity, should be constructed of a material capable of maintaining its structural integrity and the integrity and patency of the vessel in which it is inserted for a period of time necessary to complete the surgical anastomosis procedure. In addition, it is preferred to have the stent dissolve over a period of time sufficient to avoid problems or complications associated with vessel blockage caused when the stent is inserted. Preferably, the stent is constructed of a material which substantially completely dissolves over a period of time to be determined by the particular use and environment of the stent, which may vary from about 10 minutes to about 10 hours and, more preferably, about 10 minutes to about 1 hour. One presently preferred biocompatible, non-toxic material of which the dissolvable stent is constructed comprises a crystallized saccharide, although one skilled in the art will appreciate that other dissolvable, biocompatible, non-toxic materials may be used in accordance with the present invention. The presently preferred saccharide comprises sucrose, although other saccharides may be used in accordance with the present invention.

Saccharides, and sucrose in particular, are easy to work with and are relatively inexpensive. It may be desired, however, to include additional binders, such as gelatin and cellulose, for example, and/or fillers, such as sorbitol and dicalcium phosphate, for example, and/or excipients, such as silica, stearic acid, citric acid and magnesium stearate, for example, to achieve the desired hardness and dissolving time.

The dissolvable stent 10 according to the present invention is manufactured by dissolving the biocompatible, non-toxic solid material in a biocompatible, non-toxic liquid at a temperature sufficient to form a liquid solution. For example, where the non-toxic solid material comprises sucrose, the non-toxic liquid used may be water. Depending on the concentration of the solution desired, the solid and liquid mixture may be heated to allow the solid material to dissolve. The liquid solution is then poured into molds (not shown) having shapes complementary to the member components of the stent 10 to form the various member components of the stent 10. One skilled in the art will readily appreciate in view of this disclosure that many different molds may be used in the manufacture of a dissolvable stent 10 in accordance with the present invention, such as metal (aluminum, e.g.), plastic and other materials depending on the temperature of the solution to be poured into the mold and the intricacy of the shape desired, among other factors.

The liquid solution is then allowed to solidify in the molds to form the members comprising the stent 10 according to the present invention. The solidified members are then removed from the mold and are ready for use in anastomosis procedures or may be stored in appropriate storage facilities for future use.

The overall shape and dimensions of the stent 10 according to the present invention will vary depending on the intended anastomosis use, such as end-to-end, isoperistaltic, side-to-side, antiperistaltic, side-to-end and end-to-side anastomoses. The dimensions of the stent 10 will also vary depending on the size of the vessel or vessels undergoing anastomosis, such as the intestine, stomach, gallbladder and blood vessels, among others.

For illustrative purposes, the various embodiments of the stent as illustrated in the drawings are intended for use in end-to-end intestinal anastomosis procedures. Preferably, the male member 12 has a first end 14 having a first circumference and an integrally formed second, projecting end 16 having a second circumference smaller than the first circumference. Preferably also, the female member 20 has a first end 24 having an outer circumference substantially the same as the first circumference of the first end 14 of the male member 12 and a inner circumference 22 that at least partially receives the second end 16 of the male member 12.

The first end 14 of the male member 16 preferably has a tapered end portion 15. The female member 20 has a second end 26 which preferably is also tapered. The tapered portions or ends of the male aid female members and in the insertion of the male and female members into the respective vessel stumps. If desired, as illustrated in the embodiment of FIG. 3b, the male and female members 12' and 20', respectively, have a truncated tapered shape extending from their first ends 14' and 24', respectively, to their second ends 15' and 26', respectively. In addition, the male and female members (12, 20) are generally circular in cross-section to accommodate and adapt to the general shape of the lumen of the vessel undergoing anastomosis.

It is preferred in accordance with the present invention that the female member 20 receive the male member 12 in a generally friction free manner so that the male member 12 is slidingly removable from the cavity 22 of the female member 20. Thus, as discussed below in further detail, when compressive force on the two stent members is released, the stent members may separate relatively freely, thereby reducing the force at the anastomosis site. The circumference of the second end 16 of the male member 12 is slightly less than the inner circumference of the cavity 22 of the female member to allow the second end 16 to fit and move freely within the female member 20. The stent 10 according to the present invention as illustrated in FIG. 3c is constructed to have two hollow female members 36 and 42 having cavities or bores 38 and 40, respectively, which slidingly engage a central core 44 functioning as the second projecting end 16 or 16' of male members 12 and 12' of FIGS. 3a and 3b, respectively. One skilled in the art will appreciate that a stent according to the present invention may be constructed to have other configurations depending on the particular anastomosis procedure desired to be performed using the stent 10.

Especially in intestinal anastomoses, there must be complete mucosa to mucosa (outer vessel surface to outer vessel surface) contact to have an effective surgical procedure. Accordingly, the dissolvable stent 10 of the present invention is configured to allow for introflection of the edges of the vessel stumps during surgical anastomosis procedures. Thus, as illustrated in FIG. 4, the circumference of the second, projecting end 16 of the male member 12 is sufficiently smaller than the circumference of the first end 14 of the first or male member 12 and the outer circumference of the second or female member 20 to allow annular introflection of vessel stump edges at a position between the male and female members. The introflected edges of the vessel stumps are temporarily clamped between the face 17 of the male member 12 and the adjacent face 21 of the female member 20.

The difference between the circumferences of the first and second ends may be expressed as a ratio of the circumference of the first end 14 of the first or male member 12 (or first member 36) to the circumference of the second, projecting end 16 of the male member 12 (or core 44) of the stent 10 and is sufficiently large to allow for introflection of the vessel stump edges and sufficiently small to avoid ischemia, necrosis and fibrosis causing substenosis or stenosis (partial or acute occlusion of the vessel lumen). It is preferred that the ratio of the circumference of the first end 14 of the male member 12 to the circumference of the second end 16 of the male member 12 is about 4.0:1 to about 1.25:1. A ratio of about 2:1 is presently preferred. One skilled in the art will readily appreciate that the ratio between the first and second circumferences of the ends 14, 16 of the male member 12 may be greater or less depending on the type, size, and wall thickness of the vessel into which the stent 10 is to be inserted.

Further in accordance with the present invention, surgical mammalian vessel anastomosis connecting a first vessel stump 120 and a second vessel stump 200 as illustrated in FIGS. 1, 4 and 5, comprises circumferentially inserting purse-string sutures (122, 202) into the first and second vessel stumps (120, 200) respectively, to assist introflection of the vessel stumps edges during the procedure. Conventional suturing techniques may be used, such as those disclosed by T. G. Hardy et al., "Initial Clinical Experience With a Biofragmentable Ring for Sutureless Bowel Anastomosis," *Dis. Col. & Rect.*, 30:55 at 58.

Once the vessel stumps have been sutured, the first end 14 of the male member 12 is inserted into the opening of the first vessel stump 120 and the second end 26 of the female member 20 is inserted into the opening of the second vessel stump 200 as illustrated in FIG. 2. The second end 16 of the male member 12 is then partially inserted into the cavity 22 at the first end 24 of the female member 20. The purse-string sutures (122, 202) are then tightened to annularly introflect the edges of the first and second vessel stumps (120, 200) onto the second end 16 of the male member 12 of the stent 10. The sutures do not need to be tied.

With the male and female members of the stent 10 axially aligned, the second end 16 of the male member 12 is inserted farther into the female member 20 to cause the annularly introflected edges of the first and second vessel stumps to engage, forming a substantially annular engagement region. This may be done by applying an axial force on the ends of the stent members with surgical apparatus as illustrated in FIGS. 6 through 11 or the surgeon's hand as illustrated in FIGS. 4 and 5 and applying a compressive force sufficient to hold the introflected edges in substantially complete engagement. The stent members are brought together with a clamping force sufficient to maintain the edges of the stumps in annular engagement region 30 between the faces 17 and 21 of the male and female members, respectively.

While maintaining the annular engagement region 30 under compressive forces, a biocompatible sealant 32 is preferably applied to the external surfaces of the first and second vessel stumps (120, 200) in an amount sufficient to substantially entirely cover the engagement region as illustrated in FIG. 5. It is preferred that the purse-string sutures (122, 202) are then removed from the vessel stumps (120, 200) while the introflected ends of the vessel stumps are clamped together, although it is possible to remove the purse-string sutures (122, 202) prior to applying the biocompatible sealant 32. It will be appreciated by one skilled in the art that, where the purse-string sutures (122, 202) are removed (either before or after the sealant 32 is applied), the biocompatible sealant 32 is applied in a manner sufficient to cover any holes in the vessel stumps left after removing the sutures.

Once the sealant 32 has solidified or cured sufficiently to maintain adhesion at the annular engagement region 30, the compressive force on the stent members may be released and the stent 10 may, if desired, be moved away from the anastomosis site or even removed, where, for example, the stent was applied using an insertion device 50 such as the modified intraluminal stapler systems illustrated in FIGS. 6 through 8 and FIGS. 9 through 11.

The biocompatible sealant may comprise any non-toxic sealant which can effectively hold and seal living tissue in the mammalian body. One example of a presently preferred biocompatible sealant is a fibrin sealant comprising fibrinogen and thrombin commercially available as the TISSUCOL TM sealant manufactured by Immuno AG, Vienna, Austria. Another example of a suitable biocompatible sealant is described by T. Kamiji et al., "Microvascular Anastomosis Using Polyethylene Glycol 4000 and Fibrin Glue," *Brit. J. Plas. Surg.*, 42:54-58 (1989). In view of the present disclosure, one skilled in the art will appreciate that other biocompatible sealants presently available and those which may be developed may also be used to seal the vessel stumps.

In view of this disclosure, it will be appreciated that the dissolvable stent for mammalian anastomoses according to the present invention may be used to provide intraluminal support during anastomosis procedures and to provide compression forces to hold the introflected portions of the vessel stumps in an engaged position for only the time necessary to permit the application and solidification or curing of a biocompatible sealant, rather than providing a conventional anastomosis stent which maintains compressive forces on the engagement region for considerably longer periods of time. Such reduced compression time helps to avoid ischemia, necrosis or fibrosis with resulting substenosis or stenosis, which are typical complications associated with conventional anastomosis stents and techniques.

In addition, the stent according to the present invention is substantially completely dissolvable in mammalian bodily fluids and is constructed of a biocompatible material, thereby avoiding the implantation of foreign objects in vivo, avoiding possible blockage problems associated with conventional anastomosis stents and virtually eliminating discomfort associated with the passing of conventional stent fragments or anastomosis buttons.

Further, using the anastomosis stent according to the present invention, a significantly improved anastomosis procedure may be performed allowing the removal of purse-string sutures which, in conventional anastomosis procedures, typically caused increased necrosis, ischemia and edema. The removal of such purse-string sutures thus eliminates another foreign body from the site of the surgical procedure.

The invention will now be illustrated in further detail by reference to the following specific, non-limiting examples. While the examples discussed below were performed on intestinal vessels, it will be readily appreciated by one skilled in the art that the present invention may be readily modified for anastomoses of other vessel organs.

EXAMPLE 1

A two piece intestinal stent intended for use in intestinal anastomoses in pigs was prepared from a sucrose and water mixture. Granular sucrose was added to heated water in a beaker until the mixture was approximately a 2:1 by weight ratio of sucrose to water. The mixture was heated to approximately 250° F. and stirred until the sucrose dissolved. The sucrose and water mixture was slowly poured into molds formed from 0.01 millimeter sheets of aluminum. The stent intended for use in the colon was initially formed in three parts: (1) the second end of the male member or shaft-shaped member measured approximately 40 millimeters in length, 17 millimeters in diameter and appeared generally circular in cross-section; (2) the first end of the male member measuring approximately 27 millimeters in diameters at its largest point and tapering distally to a diameter of approximately 17 millimeters; and (3) a corresponding female member having the same dimensions as the first end of the male member. Stents intended for use in the small intestine had correspondingly smaller dimensions.

The water and sucrose mixture was poured into the shaft mold and cooled until the shaft was hardened. The sucrose and water mixture was then poured into the male and female member molds. Approximately 3-5 minutes after pouring the mixture into the male member mold, the hardened shaft member was inserted approximately 20 millimeters into the semi-hardened male member mold and stabilized vertically while hardening continued. A hollow or solid 18 millimeter diameter tube was inserted into the female member mold to form an inner cavity having a circumference for at least partially receiving the second end of the male member. The hollow or solid tube was twisted occasionally to keep it from becoming solidified in the female member mold. When semi-hardening of the female member mold was observed (marked by the formation of large crystals or free rotation of the hollow or solid tube without deformation of the surrounding semi-hardened stent upon rotation of the hollow tube), the tube was withdrawn. After cooling, the stents were stored at 4° C.

EXAMPLE 2

80 female Landrace pigs weighing approximately 25 to 35 kilograms were used to perform 80 anastomoses—40 with the dissolvable stent according to Example 1 of the present invention and fibrin sealant; 40 controls with 4-0 (colon) and 5-0 (small intestine) reabsorbable sutures. Premedication included a mixture of atropine (i.m. 0.01 mg/kg of body weight) and ketamine (2.5 mg/kg). Anesthesia was induced using a mixture of halothane (0.5%-1.0%) and $NO_2$ (70%) with remaining percentage $O_2$ using a face mask with spontaneous breathing. Intravenous infusion (auricular vein) of 5%-10% glucose (300-500 ml) or physiologic solution was employed for the length of the operation to permit intravenous drug administration (ketamine, e.g.) and atropine when needed.

The anastomosis procedure began with a mid-line abdominal incision long enough to localize the intestinal loop to be worked on. The segment of the intestine where the anastomosis was to be performed was then mobilized. Purse-string sutures were inserted above and below the anastomosis site. Cutting and cauterization of the intestine walls. was done slowly and layer-by-layer to reduce the phenomenon of bulging tissue. Using a stent prepared according to the procedure of Example 1, the stent members were inserted into the stumps. The second end of the male member of the stent was then inserted into the female member of the stent and the two purse-string sutures were tightened to introflect the stump edges onto the second end of the male member. The stent was then closed to compress the introflected edges of the stumps together using pressure from the thumb and index finger. TISSUCOL TM sealant was then applied, the purse-string sutures were removed and a second layer of sealant was applied to cover the suture holes. Pressure was maintained for approximately 6 to 7 minutes. The stent was then gently pushed away from the anastomosis to check the patency of the lumen.

The animals were brought out of anesthesia by ceasing halothane administration approximately 10 minutes before the end of the operation and lowering the $NO_2$ level and then stopping it at closure. The animals were then maintained on $O_2$ until the first signs of movement. Postoperatively, the animals were starved for the first postoperative day and received a mush (regular chow mix with water) the second day. Regular feeding was resumed on the third postoperative day.

There were no intraoperative deaths and no postoperative deaths. No unusual changes in bowel function were noted and there were no significant clinical differences between those animals undergoing the anastomosis procedure in accordance with the present invention versus the control procedures. Macroscopic examination of the pigs at 7, 14, 21, 30, 45, 60 and 120 days indicated no significant difference in adhesion or edema occurrence at the anastomosis sites in the experimental pigs versus the control pigs, indicating the success of the experimental procedures. Further, during macroscopic inspection, the anastomosis lines were difficult to see in the non-control animals without the aid of markers (sutures) on the intestinal serosa or a microscope at 21, 30, 45, 60 and 120 days. Microscopic examination showed less occurrence of granulation tissue in the experimental pigs than in the control pigs. The decreased granulation tissue occurrence in the experimental pigs indicated fewer infections at the anastomosis site and, I believe, this is due to the absence of foreign bodies, such as sutures, in the anastomosed vessels.

It will appreciated by those skilled in the art that the present invention may be embodied in other specific forms without departing from the spirit or essential attributes thereof and, accordingly, a reference should be made to the appended claims, rather than the foregoing specification, as indicating the scope of the invention.

I claim:

1. A dissolvable stent for mammalian anastomoses comprising a first member for receiving a first vessel stump, a second member for receiving a second vessel stump, and engaging means for engaging the first and second members, the first and second members and the engaging means being constructed of a biocompatible, non-toxic material which substantially completely dissolves in mammalian bodily fluids, wherein the first and second members each has a cavity extending at least partially therethrough along a longitudinal axis thereof and the engaging means is longitudinally insertable at least partially in the cavities.

2. The stent according to claim 1, wherein the engaging means is integrally formed with the first member forming a male member and the second member being a female member, the male member being engageable with the female member.

3. The stent according to claim 1, wherein the dissolving, biocompatible, non-toxic material substantially completely dissolves over a period of time of about ten minutes to about five hours.

4. The stent according to claim 1, wherein the dissolving biocompatible, non-toxic material comprises a crystallized saccharide.

5. The stent according to claim 4, wherein the saccharide is sucrose.

6. A method of surgical mammalian vessel anastomosis connecting a first vessel stump having an external surface and a generally annular opening to a second vessel stump having an external surface and a generally annular opening using a dissolvable stent, the stent comprising a male member for receiving a first vessel stump, the male member having a first end with a first circumference and a second end with a second circumference smaller than the first circumference, and a female member for receiving a second vessel stump, the female member having first and second ends, an outer circumference at least partially substantially the same as the first circumference of the male member and an inner circumference for at least partially receiving the second end of the male member, the male and female members of the stent being axially aligned when the second end of the male member is received by the female member, the method comprising the steps of:

(a) circumferentially inserting a first purse-string suture into the first vessel stump and circumferentially inserting a second purse-string suture into the second vessel stump, the first and second purse-string sutures being positioned proximate edges of the first and second vessel stumps;

(b) inserting the first end of the male member of the stent into the opening of the first vessel stump and inserting the second end of the female member of the stent into the opening of the second vessel stump;

(c) inserting the second end of the male member of the stent partially into the first end of the female member of the stent;

(d) tightening the purse-string sutures to annularly introflect the edges of the first and second vessel stumps onto the second end of the male member of the stent;

(e) inserting the second end of the male member of the stent farther into the female member of the stent to cause the annularly introflected edge of the first vessel stump to engage the annularly introflected edge of the second vessel stump to form a substantially annular engagement region between the male and female members with a clamping force sufficient to maintain the edges of the stumps in the annular engagement region;

(f) applying a biocompatible sealant to the external surfaces of the first and second vessel stumps to substantially entirely cover the substantially annular engagement region; and (g) removing the purse-string sutures from the first and second vessel stumps.

7. The method according to claim 6, further comprising reapplying the biocompatible sealant to cover any holes in the vessel stumps left after removing the purse-string sutures.

8. The method according to claim 6, wherein the biocompatible sealant is fibrin glue.

9. The method according to claim 8, wherein the biocompatible sealant is fibrin glue consisting of fibrinogen and thrombin.

10. The method according to claim 6 wherein the mammal is a human.

11. The method according to claim 6, wherein the mammalian vessel is an intestine.

* * * * *